(12) United States Patent
Brandt

(10) Patent No.: US 8,287,924 B2
(45) Date of Patent: Oct. 16, 2012

(54) TREATMENT OF MENOPAUSAL SYMPTOMS AS NOVEL INDICATION FOR MYRRH

(75) Inventor: Eva Brandt, Gemuenden/Wohra (DE)

(73) Assignee: Sonia Pharma GmbH, Gemuenden/Wohra (DE)

( * ) Notice: Subject to any disclaimer, the term of this patent is extended or adjusted under 35 U.S.C. 154(b) by 0 days.

(21) Appl. No.: 13/050,225

(22) Filed: Mar. 17, 2011

(65) Prior Publication Data

US 2012/0237621 A1    Sep. 20, 2012

(51) Int. Cl.
*A61K 36/00* (2006.01)
*A61K 36/328* (2006.01)

(52) U.S. Cl. ........................... 424/748; 424/725

(58) Field of Classification Search ........................ None
See application file for complete search history.

(56) References Cited

U.S. PATENT DOCUMENTS

| | | | |
|---|---|---|---|
| 4,592,912 A | 6/1986 | Nickolaus | |
| 4,719,111 A | 1/1988 | Wilson | |
| 5,248,503 A | 9/1993 | Emanuel-King | |
| 5,273,747 A | 12/1993 | Bombardelli et al. | |
| 5,350,774 A | 9/1994 | Palou | |
| 5,690,948 A | 11/1997 | McCook et al. | |
| 5,972,341 A | 10/1999 | Andre et al. | |
| 6,019,975 A | 2/2000 | Bajor et al. | |
| 6,077,513 A | 6/2000 | Massoud | |
| 6,086,889 A | 7/2000 | Agarwal et al. | |
| 6,113,949 A | 9/2000 | Brink | |
| 6,630,177 B1 | 10/2003 | Andre et al. | |
| 6,896,901 B2 | 5/2005 | Pratap et al. | |
| 2003/0170325 A1 | 9/2003 | Mermelstein et al. | |
| 2005/0037033 A1* | 2/2005 | Camus-Bablon et al. | 424/400 |
| 2005/0158411 A1* | 7/2005 | Vail et al. | 424/747 |
| 2007/0178169 A1* | 8/2007 | Fochesato | 424/539 |

FOREIGN PATENT DOCUMENTS

| | | | |
|---|---|---|---|
| CN | 1113150 A | * | 12/1995 |
| CN | 1559586 A | | 1/2005 |
| CN | 1679687 A | | 10/2005 |
| CN | 1745837 A | * | 3/2006 |
| CN | 101057892 A | | 10/2007 |
| CN | 101849981 A | | 10/2010 |
| WO | 9842188 A1 | | 10/1998 |
| ZA | 20000192 | | 1/2000 |

OTHER PUBLICATIONS

Marongiu et al., "Chemical Composition of the Essential Oil and Supercritical CO2 Extract of *Commiphora myrrha* (Nees) Engl. and of *Acorus calamus* L.", J. Agric. Food Chem., 2005, pp. 7939-7943, vol. 53.
Dolara et al., "Local Anaesthetic, Antibacterial and Antifungal Properties of Sesquiterpenes from Myrrh", Planta Medica 66, 2000, pp. 356-358.
United States Pharmacopeia / National Formulary / Myrrh, May 1, 2009.
Bauer, Color Atlas of Colposyopy, 5th Edition, 1998, pp. 92 and 115, Schattauer, Stuutgart, Germany.
Schmidt-Matthiesen, Gynecology and Obstetrics, 10th Edition, 2005, pp. 346-349, Schattauer, Stuutgart, Germany.
Massoud et al., Mirazid in Treatment of Human Hymenolepiasis, J. Egypt. Soc. Parasitol., 2007, pp. 863-876, vol. 37, No. 3.
Sturdee et al., Recommendations for the management of postmenopausal vaginal atrophy, Climacteric, 2010, pp. 1-14.
Database WPI Week 200626, Thomson Scientific, London, GB, Oct. 12, 2005, (XP002656178) (Abstract for CN 1679687).
Database WPI Week 201108, Thomson Scientific, London, GB, Oct. 6, 2010, (XP002674663) (Abstract for CN 101849981).
Database WPI Week 200825, Thomson Scientific, London, GB, Oct. 24, 2007, (XP002656179) (Abstract for CN 101057892).
Database WPI Week 200113, Thomson Scientific, London, GB, Sep. 27, 2000, (XP002656181) (Abstract for ZA 200000192).

* cited by examiner

*Primary Examiner* — Qiuwen Mi
(74) *Attorney, Agent, or Firm* — The Webb Law Firm

(57) ABSTRACT

A novel medical indication of myrrh, namely the treatment of menopausal symptoms, is disclosed. Furthermore, pharmaceutical preparation in vaginal dosage form for the treatment of menopausal symptoms, a method for preparing a pharmaceutical preparation against menopausal symptoms, and a method for treating the human or animal body with myrrh to relieve menopausal symptoms are disclosed.

13 Claims, No Drawings

TREATMENT OF MENOPAUSAL SYMPTOMS AS NOVEL INDICATION FOR MYRRH

BACKGROUND

The instant invention relates to a novel indication for myrrh, a pharmaceutical preparation in vaginal dosage form, a method for preparing a pharmaceutical preparation against menopausal symptoms, and a method for treating the human or animal body with myrrh to relieve menopausal symptoms.

Myrrh Resin

Myrrh is the oleo-gum resin obtained from stems and branches of *Commiphora molmol* Engler and other related species of *Commiphora* other than *Commiphora mukul*. *Commiphora mukul*—although sharing the genus name—cannot be used for obtaining myrrh. *Commiphora molmol* Engler is sometimes also referred to as *Commiphora myrrha* or *Commiphora myrrha* (Nees) Engler. Suited related species of *Commiphora molmol* for obtaining myrrh are *Commiphora abyssinica* Engler and *Commiphora schimperi* Engler. Pharmacopoeia myrrh is generally obtained from *Commiphora molmol* Engler, but the other related species, in particular those referred to above, are also well suited.

For medical purposes, myrrh is used as powdered resin, capsules, myrrh tincture and other galenical preparations for topical use.

Myrrh can be separated into three components: volatile oil (ca. 2 to 10%), alcohol-soluble resin (ca. 25 to 40%) and water-soluble gum.

The main constituents of myrrh essential oil are furanosesquiterpenes of various structural types together with sesquiterpenes. Furanosesquiterpenes are the source of its characteristic balsamic odour; a mixture of furanoeudesma-1,3-diene and lindestrene has the typical aroma of myrrh.

Myrrh essential oil is generally obtained by hydrodistillation, steam distillation, and solvent extraction. Extraction by carbon dioxide in the supercritical state is the state-of-the-art process that offers many advantages in obtaining volatile extracts. The mild extraction conditions give assurance against chemical reactions not taking place during the process; i.e. no hydrolysis, oxidation, or isomerisation taking place. Other possible extraction agents include nitrogen, hexane, methane, and ethane.

Marongiu et al.: "Chemical Composition of the Essential Oil and Supercritical $CO_2$ Extract of *Commiphora myrrha* (Nees) Engl. and of *Acorus calamus* L.", J. Agric. Food Chem. 53 (2005), 7939-7943 discloses the composition of myrrh extract obtained by different methods. The authors demonstrated that hydrodistillation (HD), steam distillation (SD) and supercritical extraction with carbon dioxide (SFE) yield similar results as far as main components and quantities extracted are concerned.

Myrrh is known for its wound healing effect. Dolara, P. et al.: "Local Anaesthetic, Antibacterial and Antifungal Properties of Sesquiterpenes from Myrrh", Planta Medica 66 (2000), 356-358 describe the anaesthetic, antibacterial and antifungal properties of certain sesquiterpenes of myrrh.

U.S. Pat. No. 4,719,111 A discloses the external use of myrrh gum for treating decubitus ulcers.

U.S. Pat. No. 4,592,912 A discloses the topical use for the relief of or for the prevention of muscular aches, pains, cramps and muscular spasms such as are found, for example, in overexerted muscles, misused muscles, headaches and back aches.

U.S. Pat. No. 5,350,774 A describes the topical treatment of skin disorders with myrrh.

U.S. Pat. No. 5,248,503 A discloses the utilization of myrrh as food or dietary supplement.

U.S. Pat. No. 6,077,513 A discloses a pharmaceutical composition containing myrrh oil and myrrh resin as the active ingredients therein for treating schistosomiasis.

Physiology of Menopausal Vaginal Symptoms

The menopause is defined as the permanent cessation of cyclical menstruation due to loss of ovarian follicular activity. The decline in estrogen concentration is associated with both acute and long-term effects. Established acute symptoms are vasomotor instability, manifesting as hot flushes and night sweats, and vaginal atrophy, manifesting as vaginal dryness, itching, burning, and discomfort.

Menopausal symptoms may be managed by using hormone replacement therapy (HRT) with estrogens, with or without progestogens. Adverse effects of HRT include an increased risk of breast cancer, ovarian and endometrial cancer, an increased risk of venous thromboembolism, stroke, dementia, gallstone formation and cholecystectomy. It is now generally recommended that menopausal HRT used to relieve vasomotor and vaginal symptoms should be given at the lowest effective dose for no longer than necessary. But to withdraw HRT means recurrence of menopausal symptoms.

Density of estrogen receptors is highest in endometrium and vagina. A drop in estrogen levels results in
- a decrease in mitotic activity, so the vaginal lining becomes thinner and more fragile;
- a drop in collagen content in the connective tissue;
- decreased blood flow and decreased vaginal lubrication;

leading to vaginal symptoms and findings of pallor, dryness and decreased rugosity of the vaginal mucosa.

US 2003/0170325 A1 discloses compositions in gel or suppository form for the treatment of vaginal dryness. The compositions comprise herbal compounds with or without vitamin. However, this patent application does not suggest using extracts of myrrh for the treatment of vaginal dryness.

SUMMARY

A non-hormonal effective treatment of menopausal symptoms is needed, as an alternative to HRT. It is an objective of the instant invention to provide an active ingredient for a pharmaceutical preparation or a medicinal product for such a treatment, a pharmaceutical preparation in a suitable dosage form as well as a method for preparing a pharmaceutical preparation against menopausal symptoms.

This objective is achieved by using myrrh for the treatment of menopausal symptoms according to claim 1. In the patent and non-patent literature known to the inventor, no teaching or suggestion for such an indication of myrrh could be found. This novel indication is surprising since menopausal symptoms are not related to bacteria and fungi against which myrrh has been used hitherto.

The term "myrrh" is to be understood as the oleo-gum resin originating from *Commiphora* species with the exception of *Commiphora mukul*. In an embodiment, the myrrh is pharmacopeia myrrh.

The term "menopausal symptoms" relates to all symptoms occurring in the menopause. Established acute symptoms are vasomotor instability, manifesting as hot flushes, and vaginal atrophy, manifesting as vaginal dryness, itching, burning, and discomfort.

In an embodiment, the myrrh is present in the form of a powdered resin, a myrrh tincture or an extract of myrrh.

In another embodiment, the extract of myrrh is a dry extract (which can be obtained by extraction of myrrh with an organic solvent) or an aqueous extract. In a further embodiment, the myrrh is used in pastry form. To obtain a pastry, myrrh resin is subjected to extraction with an organic solvent, for example ethanol, petroleum ether or ethyl acetate. The extract thus obtained is filtered and vacuum-concentrated to a pastry form. Thus, myrrh pastry is a filtered and concentrated form of a myrrh extract. The residue is again dissolved in alcohol (e.g., ethanol) or a mixture of alcohol and water, filtered and vacuum-concentrated.

In a further embodiment, the myrrh is used as lipophilic extract of myrrh, in particular obtained by extraction with liquid carbon dioxide in the supercritical state. Other standard extraction methods as explained above are also applicable.

In a further embodiment, the extract contains furanoeudesma-1,3-diene, lindestrene and curzerene as main ingredients. The according chemical structures of these compounds are displayed below:

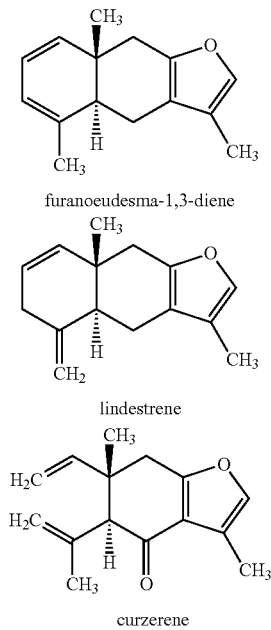

furanoeudesma-1,3-diene lindestrene curzerene

In an embodiment, furanoeudesma-1,3-diene is present in the extract in an amount of more than 20%, in particular more than 25%, in particular more than 30% and very particular more than 35%. All percentages given in the present application are to be understood as percent by weight if not explicitly indicated otherwise.

In a further embodiment, the extract contains more than 10%, in particular more than 15%, in particular more than 20% and in particular more than 25% of curzerene.

In a further embodiment, the extract contains more than 5%, in particular more than 10%, in particular more than 15% of lindestrene.

In a further embodiment, the extract has a refractive index at 20° C. (measured with an Abbe refractometer) of 1.5 to 1.6, in particular of 1.51 to 1.55, in particular of 1.515 to 1.54, in particular of 1.517 to 1.537.

In a further embodiment, the extract has a density at 20° C. (measured with a pycnometer) of 1.0 to 2.0 g/cm$^3$, in particular of 1.02 to 1.08 g/cm$^3$, in particular of 1.025 to 1.075 g/cm$^3$.

In a further embodiment, the menopausal symptoms comprise vaginal atrophy. In an embodiment, the symptoms exclusively consist of vaginal atrophy. In other words, the myrrh is well suited for the treatment of vaginal atrophy and symptoms related therewith occurring (not exclusively but also) during menopause.

In a further embodiment, the myrrh is present in a semisolid dosage form for vaginal application, in particular as vaginal ointment, vaginal cream, or vaginal gel. In such semisolid preparations, oleaginous bases or water-soluble bases can be used. The semisolid preparations might be water-in-oil emulsions or oil-in-water emulsions.

In yet another embodiment, the myrrh is present in a liquid dosage form for vaginal application, in particular as vaginal liquid, vaginal emulsion, or vaginal suspension.

In another embodiment, the myrrh is present as vaginal foam or vaginal tampon.

In still another embodiment, the myrrh is present in a solid dosage form for vaginal application, in particular as vaginal tablet, vaginal capsule, or vaginal suppository.

Any of the afore-mentioned vaginal dosage forms enables a user to apply the myrrh at the location at which it can develop its activity against menopausal symptoms in a very well suited manner.

In a further embodiment, the solid dosage form, in particular the vaginal tablet, vaginal capsule, or vaginal suppository essentially consists of a fatty, oleaginous, or oil-type base and the myrrh. Cocoa butter and hard fat are members of this group of substances. Cocoa butter is an oleaginous base that softens at 30° C. and melts at about 34° C., just below body temperature, thus representing an ideal suppository base. Other bases in this category include commercial products such as Fattibase (triglycerides from palm, palm kernel, and coconut oils with self-emulsifying glyceryl monostearate and polyoxyl stearate), Wecobee bases (triglycerides derived from coconut oil), Witepsol bases (triglycerides of saturated $C_{12}$-$C_{18}$ fatty acids with varying portions of the corresponding partial glycerides), Suppocire and Ovucire bases)

The inventor could already establish a synergistic effect of the combination of cocoa butter and myrrh. In particular, experiments indicate that constituents of cocoa butter and ingredients of myrrh essential oil show synergistic effects on mitotic activity, collagen metabolism, blood flow or lubrication when applied vaginally for treatment of vaginal atrophy. Thus, using cocoa butter as basic material even enhances the effectivity of the myrrh.

It was found that a very well suited dosage for using the myrrh, in particular in form of a suppository, is daily, in particular once a day, in particular once a day at bed time. Such a dosage regime is sufficient to alleviate the menopausal symptoms, in particular vaginal atrophy.

An aspect of the invention also relates to a pharmaceutical preparation or medicinal product in vaginal dosage form, in particular a vaginal ointment, a vaginal cream, a vaginal gel, a vaginal liquid, a vaginal emulsion, a vaginal suspension, a vaginal foam, a vaginal tampon, a vaginal tablet, a vaginal capsule, or a vaginal suppository containing myrrh as pharmaceutical active ingredient.

In an embodiment, the pharmaceutical preparation is present in form of a vaginal tablet, vaginal capsule or vaginal suppository essentially consisting of a fatty, an oleaginous or an oil-type base material and myrrh according to the preceding explanations. Such a vaginal tablet, capsule or suppository is suitable for the treatment of menopausal symptoms, in particular for the treatment of vaginal atrophy and vaginal symptoms of dryness, itching, burning, and discomfort.

In an embodiment, the tablet, capsule or suppository has a weight of 0.5 to 5 g, in particular of 1 to 4 g, in particular of 2 to 3 g, in particular of 1.5 to 2.5 g, in particular of 1.7 to 1.9 g. 1.8 g is a particular well suited weight. In an embodiment, the myrrh is present in the tablet, capsule or suppository in an amount of 0.1 to 10%, in particular of 0.25 to 9%, in particular of 0.5 to 8%, in particular of 0.75 to 7%, in particular of 1 to 6%, in particular of 1.5 to 5° A), in particular of 2 to 4%, in particular of 2.5 to 3% based on the total weight of the tablet, capsule or suppository. An amount around 1% of myrrh is particularly well suited.

The objective is also solved by a method for preparing a pharmaceutical preparation or medicinal product, respectively, against menopausal symptoms, having the following steps:

melting a fatty, an oleaginous or an oil-type base at an elevated temperature above the melting temperature of this base material to obtain a melt, adding myrrh to the melt in an amount of 0.1 to 10% with respect to the sum of the base material and the myrrh so as to obtain a mixture of the base and the myrrh, stirring the mixture, pouring the mixture into at least one mould, cooling the mixture to room temperature, removing the solidified mixture from the mould.

By such a method, differently shaped pharmaceutical preparations or medicinal products against menopausal symptoms can be obtained.

In an embodiment, the mould has a shape to form the mixture such that at least one vaginal tablet, capsule or suppository is obtained. In a further embodiment, the mould forms the mixture in such a way that a plurality of tablets, capsules or suppositories is obtained. These tablets, capsules or suppositories can have the same size and/or shape or different shapes and/or sizes. Thus, differently sized and/or shaped tablets, capsules or suppositories can be provided to address the individual needs of the users of this medical product.

Explained embodiments of the claimed use of myrrh are also applicable with respect to the claimed pharmaceutical preparation and the claimed method, and vice versa.

Furthermore, a method for treating the (female) human or animal body with myrrh to relieve menopausal symptoms, in particular to relieve vaginal atrophy, is hereby disclosed.

Explained embodiments of the claimed use of myrrh or the claimed pharmaceutical preparation are also applicable with respect to this method.

Further details of aspects of the instant invention are explained in connection to the following examples which are, however, not to be construed in a limiting way.

A lipophilic extract of *Commiphora myrrha*, produced by supercritical $CO_2$ extraction, was used.

Vaginal suppositories were prepared using either hard fat or cocoa butter as suppository base.

Cocoa butter was melted at 50° C. Under stirring, myrrh extract was added to a final concentration of 1% by weight of the total weight of the formula (mixture). Stirring was continued for several hours to obtain a stable crystalline form. The mixture was then poured into molds and cooled.

Hard fat was melted at 50° C. Myrrh extract was added to a final concentration of 1% of the total weight of the formula to obtain a mixture. The mixture was poured into molds and cooled.

The suppositories weighed 2 grams each, containing 20 mg of myrrh extract each.

Both preparations (hard fat/cocoa butter) were tested in postmenopausal women (more than 2 years past last menstrual period) with vaginal symptoms of dryness, discomfort and itching. The vaginal suppositories were applied over a period of 14 consecutive days once a day, namely at bedtime each night.

Both preparations provided subjective and objective relief of menopausal symptoms, in particular vaginal symptoms. Colposcopy revealed an improved status of the vaginal mucosa.

Improvement of genital symptoms was more pronounced with the cocoa butter suppositories. *Theobroma* cocoa seeds contain polyphenols and flavonoids—substances with high antioxidation potential—and procyanidins which exhibit vascular effects. It appeared that in connection to the myrrh extract synergistic effects on mitotic activity, collagen metabolism, blood flow or lubrication occur when both substances are applied concomitantly for the treatment of vaginal atrophy.

What is claimed is:

1. A method of treating vaginal atrophy as a specific indication of menopausal symptoms comprising administering a pharmaceutical preparation in vaginal dosage form comprising myrrh to a person in need of such treatment.

2. The method according to claim 1, wherein the myrrh is present in the form of a powdered resin, a myrrh tincture or an extract of myrrh.

3. The method according to claim 2, wherein the extract of myrrh is an aqueous extract, a dry extract, or a lipophilic extract.

4. The method according to claim 2, wherein the myrrh tincture or the extract of myrrh contains furanoeudesma-1,3-diene, lindestrene and curzerene as main ingredients.

5. The method according to claim 1, wherein the pharmaceutical preparation is present in a semisolid vaginal dosage form.

6. The method according to claim 5, wherein the pharmaceutical preparation is present as ointment, cream, or gel.

7. The method according to claim 1, wherein the pharmaceutical preparation is present in a liquid vaginal dosage form.

8. The method according to claim 7, wherein the pharmaceutical preparation is present as liquid, emulsion, or suspension.

9. The method according to claim 1, wherein the pharmaceutical preparation is present as vaginal foam or vaginal tampon.

10. The method according to claim 1, wherein the pharmaceutical preparation is present in a solid vaginal dosage form.

11. The method according to claim 10, wherein the pharmaceutical preparation is present as tablet, capsule, or suppository.

12. The method according to claim 1, wherein the pharmaceutical preparation is used daily.

13. The method according to claim 12, wherein the pharmaceutical preparation is used once a day.

* * * * *